United States Patent [19]

Takeda et al.

[11] Patent Number: 5,720,946
[45] Date of Patent: Feb. 24, 1998

[54] HAIR REVITALIZING COMPOSITION CONTAINING TWO OR MORE AMINE OXIDES HAVING DIFFERENT CHAIN LINKS

[75] Inventors: Shunsuke Takeda; Masaaki Uemura; Tomiyuki Namba, all of Yokohama, Japan

[73] Assignee: Shiseido Company, Ltd., Tokyo, Japan

[21] Appl. No.: 414,308

[22] Filed: Mar. 31, 1995

[30] Foreign Application Priority Data

Mar. 31, 1994 [JP] Japan .................................. 6-085985

[51] Int. Cl.$^6$ .................................. A61K 7/08; A61K 7/06
[52] U.S. Cl. .................................. 424/70.19; 424/70.1
[58] Field of Search .................................. 424/70.1, 70.19

[56] References Cited

U.S. PATENT DOCUMENTS

| | | | |
|---|---|---|---|
| 3,098,794 | 7/1963 | Dohr et al. | 167/87 |
| 5,156,836 | 10/1992 | Uchikawa et al. | 424/70.1 |
| 5,294,644 | 3/1994 | Login et al. | 514/698 |

FOREIGN PATENT DOCUMENTS

| | | |
|---|---|---|
| 1258636 | 8/1989 | Canada . |
| 0 334 960 | 10/1989 | European Pat. Off. . |
| 0 428 754 | 5/1991 | European Pat. Off. . |
| 61-37717 | 2/1986 | Japan . |

OTHER PUBLICATIONS

*Chemical Abstracts*, vol. 117, No. 14, p. 421, abstract No. 137417v (Oct. 1992).

Miyazawa et al., *Chemical Abstracts*, vol. 117, 1991, #337417.

*Primary Examiner*—Sally Gardner-Lane
*Attorney, Agent, or Firm*—Wenderoth, Lind & Ponack

[57] ABSTRACT

A hair revitalizing composition containing as effective ingredients amine oxide compounds, in which at least two said amine oxide compounds having mutually different chain lengths are combined; a method of revitalizing hair of mammals with such a hair revitalizing composition; or use of the above compounds for preparation of the above combined hair revitalizing composition. The above composition exhibits a synergistic hair revitalizing effect, compared with cases where the two amine oxides are used independently.

10 Claims, 1 Drawing Sheet

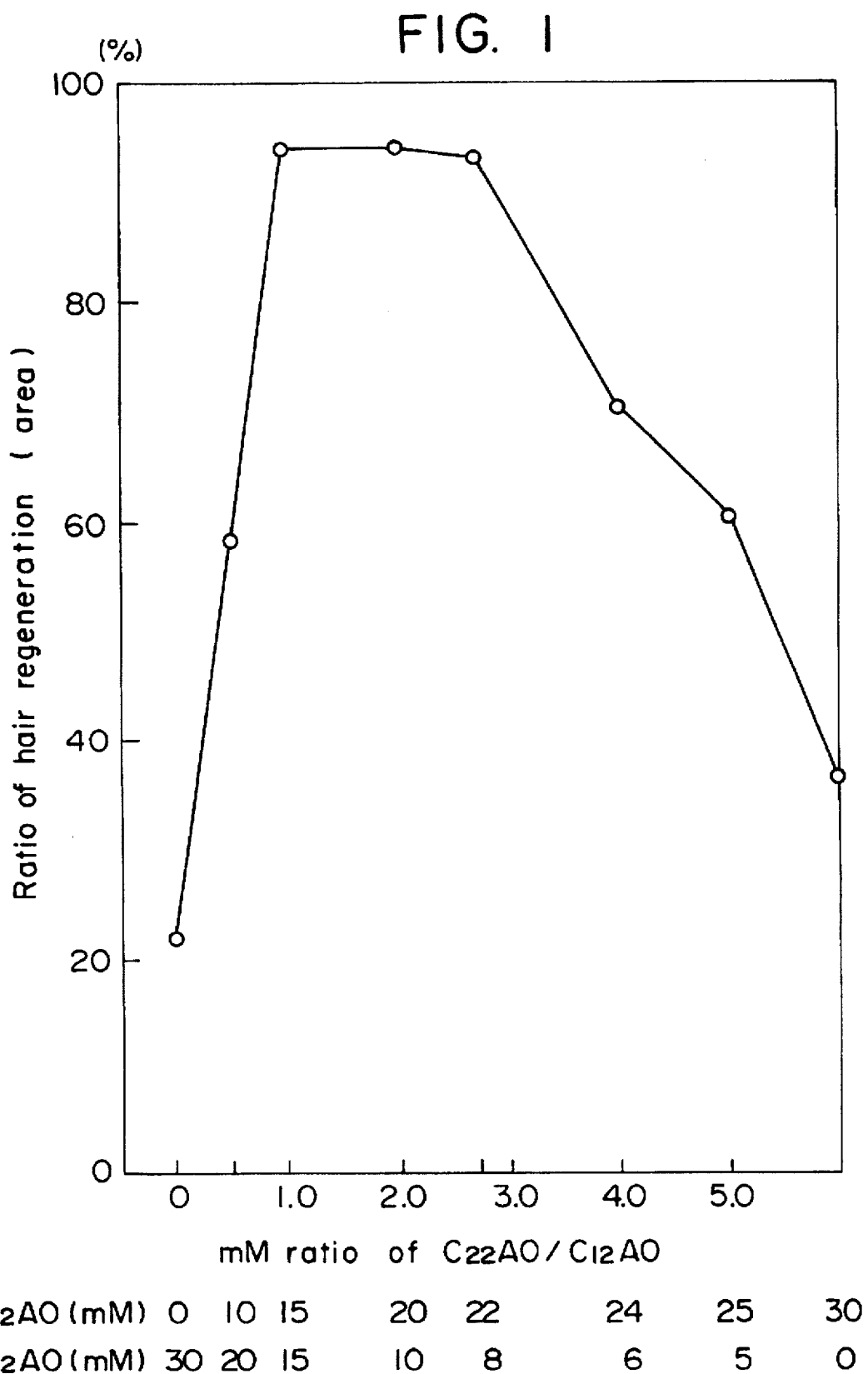

HAIR REVITALIZING COMPOSITION CONTAINING TWO OR MORE AMINE OXIDES HAVING DIFFERENT CHAIN LINKS

BACKGROUND OF THE INVENTION

1. Field of the Invention

This invention relates to a hair revitalizing composition (hair tonic composition) containing amine oxide compounds. More specifically, this invention relates to a hair revitalizing composition containing as effective ingredients two or more amine oxides having different chain lengths among amine oxides having long-chain aliphatic group(s).

2. Description of the Prior Art

Heretofore, activation of male hormones in organs such as hair root and sebum glands; lowering of bloodstream volume to hair follicles; hypersteatosis; anomaly of scalps due to formation of peroxides, etc.; etc. have been considered to be causes of baldness and hair loss. Thus, compounds having an action to remove or reduce these causes are generally incorporated in usual hair revitalizing tonics.

For example, vitamins such as vitamin Bs and vitamin Es, amino acids such as serine and methionine, vasodilators such as Swertia japonica extract, benzyl nicotinate and aceryl choline derivatives, anti-inflammatory agents such as Lithospermi Radix extract and hinokitiol, female hormones such as estradiol, skin function-raising agents such as cepharanthine, etc. are incorporated, and used for prophylaxis and treatment of alopecia.

Recently, it was published that a composition containing, in combination with an anionic surface active agent, an amine oxide having a long-chain aliphatic group, which is known to be usable for a hair conditioner composition (Japanese Unexamined Patent Publication No. 37717/1986), has an excellent hair revitalizing effect (see EP-A1-0334960 or U.S. Pat. No. 5,156,836).

Although hair revitalizing compositions having certain hair revitalizing effects are thus proposed, there still exists need for providing further effective hair revitalizing compositions. Thus the object of this invention lies in providing a hair revitalizing composition having a further excellent hair revitalizing effect, compared with usual ones.

In addition to the description that it is made to be an essential characteristic to use an amine oxide having a $C_{6-24}$ aliphatic group in combination with an anionic surface active agent, the above EP-A1-0334960 or U.S. Pat. No. 5,156,836 discloses that it is also possible to use two or more of them at the same time. However, these publications do not teach at all that what amine oxides should be used in combination and how they are combined, nor do they teach that what effects are brought about by such combination use.

The present inventors found, surprisingly, in a series of researches on hair revitalizing compositions, that when a certain kind of amine oxide is used in combination with another certain kind of amine oxide, a synergistic hair revitalizing effect is obtained only by specific compounding ratios.

SUMMARY OF THE INVENTION

According to this invention a hair revitalizing composition is provided containing as an effective ingredient a combination of at least one compound of amine oxides represented by the formula (1):

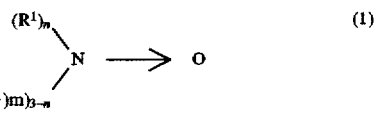

wherein $R^1$(s) are the same or different, and are each a methyl, ethyl or hydroxyethyl, $R^2$(s) are the same or different, and are each straight-chain or branched chain $C_{22-36}$ alkyl or alkenyl, n is an integer of 1 or 2, and m is 0 or an integer of 1 to 5, and at least one compound of amine oxides represented by the formula (2):

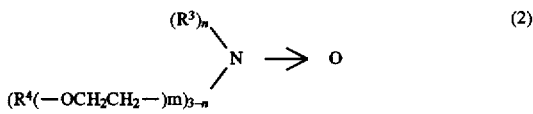

wherein $R^3$(s) are the same or different, and are each methyl, ethyl or hydroxyethyl, $R^4$(s) are the same or different, and are each straight-chain or branched chain $C_{12-20}$ alkyl or alkenyl, n and m are as defined in the formula (1), in said hair revitalizing composition, the difference in carbon numbers between the group $R^2$ of said at least one compound according to the formula (1) and the group $R^4$ of said at least one compound according to the formula (2) being 6 or more, and the ratio in molar concentrations of the compound of the above formula (1) to the compound of the above formula (2) being within the range of 0.5 to 5.

Another embodiment of this invention relates to a hair revitalizing method for a mammal which comprises applying the above hair revitalizing composition of this invention, in an effective amount for hair revitalization, to the scalp or skin of the mammal.

Still another embodiment of this invention relates to use of a specific combination of compound(s) of the formula (1) and compound(s) of the formula (2) for preparing a hair revitalizing composition.

BRIEF DESCRIPTION OF THE DRAWINGS

FIG. 1 is a graph showing that hair revitalizing compositions according to this invention exhibit a synergistic hair revitalizing effect, in a specific combination ratio between two kinds of compounds having a long-chain aliphatic group.

DETAILED DESCRIPTION OF THE INVENTION

As shown above, when one of $R^1$ and $R^2$ in the compound of the formula (1) usable in this invention denotes two groups, the other denotes one group, and when one of them denotes two groups, they can be the same or different groups. However, although not limited, when $R^1$ denotes two groups (n=2) , it is preferable that both of them are methyl groups, ethyl groups or hydroxyethyl groups, and when $R^2$ denotes two groups (n=1), it is preferable that both of them are the same straight-chain or branched chain $C_{22-36}$ alkyl groups or straight-chain or branched chain $C_{22-36}$ alkenyl groups.

$R^3$ and $R^4$ in the compound of the formula (2) can also take a similar embodiment to $R^1$ and $R^2$ in the compound of the formula (1), and when $R^3$ denotes two groups (n=2), it is preferable that both of them are methyl groups, ethyl groups or hydroxyethyl groups, and when $R^4$ denotes two groups (n=1), it is preferable that both of them are the same straight-chain or branched chain $C_{12-20}$ alkyl groups or straight-chain or branched chain $C_{12-20}$ alkenyl groups.

$R^2$ and $R^4$ can be bound to the nitrogen atoms through oxyethylene groups: ($-OCH_2CH_2-$)m, respectively, and each of the oxyethylene units in this case can be a repeating unit of 1 to 5.

Further preferred and specific examples of compounds belonging to the compound group of the formula (1) include compounds represented by the following formulae (1-a) to (1-d).

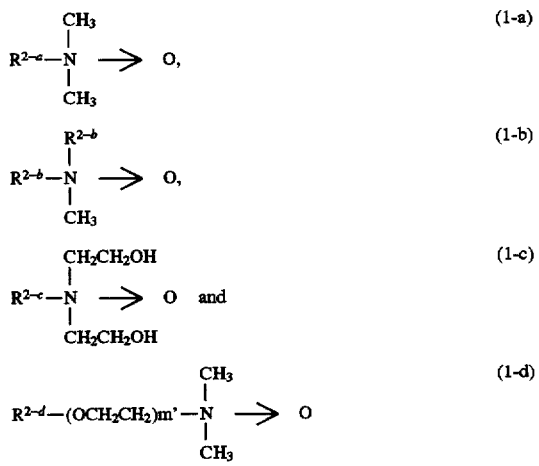

In the above formulae, $R^{2-a}$, $R^{2-b}$, $R^{2-c}$ and $R^{2-d}$ have the meanings defined for $R^2$ of the formula (1), and m' denotes an integer of 1 to 5.

On the other hand, preferred and specific examples of compounds belonging to the compound group of the formula (2) include compounds represented by the following formulae (2-e) to (2-h).

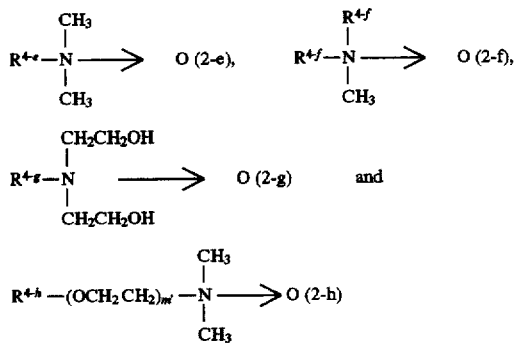

In the above formulae, $R^{4-e}$, $R^{4-f}$, $R^{4-g}$ and $R^{4-h}$ have the meanings defined for $R^4$ of the formula (2), and m' denotes an integer of 1 to 5.

Particularly preferred compounds belonging to the compound group of the formula (1) are enumerated as follows:

N,N-dimethyl-2-decyltetradecylamine oxide, N,N-dimethyl-2-dodecylhexadecyl amine oxide, N,N-dimethyl-2-tetradecylstearylamine oxide, N,N-dihydroxyethyl-2-dodecylhexadecylamine oxide, N,N-dimethyl-2-octacosylpolyoxyethylene (3 mols) amine oxide, N,N-dimethyl-2-hexacosylpolyoxyethylene (1.5 mols) amine oxide, N-ethyl-N-methyl-2-decyltetradecylamine oxide, N-ethyl-N-methyl-2-tetradecylstearylamine oxide, N-hydroxyethyl-N-methyl-octacosylpolyoxyethylene (4 mols) amine oxide, and N-ethyl-N-hydroxyethyl-2-hexadecanylpolyoxyethylene (2 mols) amine oxide.

On the other hand, particularly preferred compounds belonging to the compound group of the formula (2) are enumerated as follows:

N,N-dimethyl-2-dodeoylamine oxide, N,N-dimethyl-tetradecylamine oxide, N,N-dihydroxyethyl-hexadecylamine oxide, N,N-dimethyl-octadecylpolyoxyethylene (4 mols) amine oxide, N,N-dimethyl-eicosylpolyoxyethylene (2 mols) amine oxide, N-ethyl-N-methyl-laurylamine oxide, N-ethyl-N-methyl-tetradecanylamine oxide, N-ethyl-N-methyl-dodecanylamine oxide, N-hydroxyethyl-N-methyl-eicosylpolyoxyethylene (4 mols) amine oxide, and N-ethyl-N-hydroxyethyl-tetradecanylamine oxide.

Part of these compounds are commercially available, and these compounds can also be obtained by a preparation method known per se.

According to this invention, one or more compounds belonging to the compound group of the formula (1) are used in combination with one or more compounds belonging to the compound group of the formula (2). In the use, it is necessary for exerting the effect of this invention that the difference in carbon numbers between the group $R^2$ of the at least one compound according to the formula (1) and the group $R^4$ of the at least one compound according to the formula (2) is 6 or more. Further, it is also necessary that the ratio in molar concentration of the compound of the formula (1) to the compound of the formula (2) in the combination is within the range of 0.5 to 5.

The difference in carbon numbers between the above $R^2$ and $R^4$ is further preferably 8 to 14. On the other hand, the ratio in molar concentration of the compound of the formula (1) to the compound of the formula (2) is further preferably 0.8 to 2.5, particularly preferably 1 to 1.7.

Specific combinations between compounds belonging to the compound group of the formula (1) and compounds belonging to the compound group of the formula (2) are described below using $R^{2-a}$ and $R^{4-e}$ of the formula (1-a) and the formula (2-e), respectively. $R^{2-a}/R^{4-e}$ can, for example, be combinations of branched chain $C_{22-28}$ alkyl or alkenyl/branched chain $C_{12-16}$ alkyl or alkenyl, respectively, more specifically $C_{22}$ alkyl or alkenyl/$C_{16}$ alkyl or alkenyl, $C_{22}$ alkyl or alkenyl/$C_{15}$ alkyl or alkenyl, $C_{22}$ alkyl or alkenyl/$C_{14}$ alkyl or alkenyl, $C_{22}$ alkyl or alkenyl/$C_{13}$ alkyl or alkenyl, $C_{22}$ alkyl or alkenyl/$C_{12}$ alkyl or alkenyl, $C_{23}$ alkyl or alkenyl/$C_{16}$ alkyl or alkenyl, $C_{24}$ alkyl or alkenyl/$C_{16}$ alkyl or alkenyl, $C_{24}$ alkyl or alkenyl/$C_{15}$ alkyl or alkenyl, $C_{24}$ alkyl or alkenyl/$C_{14}$ alkyl or alkenyl, $C_{24}$ alkyl or alkenyl/$C_{13}$ alkyl or alkenyl, $C_{24}$ alkyl or alkenyl/$C_{12}$ alkyl or alkenyl, $C_{26}$ alkyl or alkenyl/$C_{16}$ alkyl or alkenyl, $C_{26}$ alkyl or alkenyl/$C_{14}$ alkyl or alkenyl, $C_{26}$ alkyl or alkenyl/$C_{12}$ alkyl or alkenyl, $C_{28}$ alkyl or alkenyl/$C_{16}$ alkyl or alkenyl, $C_{28}$ alkyl or alkenyl/$C_{14}$ alkyl or alkenyl, $C_{28}$ alkyl or alkenyl/$C_{12}$ alkyl or alkenyl, and among these combinations, those in which both aliphatic groups are branched alkyl groups are particularly preferable.

Compounds belonging to the compound group of the formula (1) and compounds belonging to the compound group of the formula (2) are compounded in a molar concentration as described above, and it is possible to incorporate each of the two kind of compounds in an amount of preferably 0.0001 to 20 weight %, more preferably 0.05 to 5 weight % per weight of the whole hair revitalizing composition. When the amount is under 0.0001 weight %, sufficient hair revitalizing effect cannot be obtained, and the amount above 20 weight % is undesirable in view of preparation of the composition or irritation to skin.

As the system of the hair revitalizing composition of this invention, there can, for example, be mentioned water, a lower alcohol (preferably ethanol, hereafter the same), a water-alcohol system (preferably alcohol 20 to 90% by weight, the balance being water), an oil, a water-oil mixture system (oil 0.2 to 80% by weight, the balance being water), an alcohol-oil mixture system (oil 0.2 to 80% by weight, the balance being alcohol), a water-alcohol-oil mixture system (alcohol 20 to 90% by weight, oil 0.2 to 80% by weight, the balance being water), a water-oil-surface active agent mixture system (oil 0.2 to 80% by weight, surface active agent 0.01 to 10% by weight, the balance being water), and a water-alcohol-oil-surface active agent mixture system (alcohol 20 to 90% by weight, oil 0.2 to 80% by weight, surface active agent 0.01 to 10% by weight, the balance being water). As the above oils and surface active agents, any of those generally used in usual hair revitalizing tonics or cosmetics can be used.

In the hair revitalizing composition according to this invention, in addition to the above components, general purpose components ordinarily used in hair revitalizing tonics can be compounded, within a range which does not impair the effect of this invention. These general purpose components include, for example, hair generating agents or hair generating aid including plant extraction extracts such as Swertia japonica extract and carrot extracts, vitamins such as vitamin B6, vitamin E and derivatives thereof and biotin, pantothenic acid and derivatives thereof, glycylrrhetic acid and derivatives thereof, nicotinic esters such as benzyl nicotinate, cyclosporins, carpronium chloride, cepharanthine, oxendolone, diazoxide, minoxidil, and ethynylestradiol; antimicrobial agents such as hinokitiol, hexachlorophen, phenol, isopropylmethylphenol, benzalkonium chloride, cetylpyridinium chloride, undecylenic acid, trichlorocarbanilide and bithionol; refrigerants such as menthol and eucalyptus oil; pharmaceuticals such as salicylic acid, zinc and derivatives thereof, and lactic acid and alkyl esters thereof; organic acids such as citric acid, succinic acid and malic acid; amino acids such as arginine; oils such as olive oil, squalane, liquid paraffin, isopropyl myristate, higher fatty acids and higher fatty alcohols; polyhydric alcohols such as glycerol and propylene glycol; other surface active agents; perfumes; antioxidants; ultraviolet absorbers; coloring matter; ethanol; water; humectants; thickeners; etc.

The hair revitalizing composition of this invention can be in any dosage form, provided that it can be applied to the outer skin, such as a liquid, an ointment, a cream, a gel or an aersol, and can be used in such a form as a tonic, a conditioner or a scalp treatment.

The hair revitalizing composition of this invention is administered by percutaneous administration to directly apply or spray to the skin or scalp. The dose of the hair revitalizing composition of this invention cannot definitely be described because the dose changes depending on ages, differences among individuals, symptoms, etc., but the dose when the composition is administered to human beings is generally 0.01 to 100 mg, preferably 0.1 to 10 mg/kg body per day, and this amount can be administered once or in divided two to four portions per day. By such treatment method, the hair revitalizing composition of this invention has, on mammals, an excellent hair loss prevention effect, a hair revitalizing effect, or an effect to prevent dandruff or itch of the skin or scalp.

EXAMPLES

Processes for preparation of the hair revitalizing composition of this invention and the hair revitalizing action (effect) thereof are further specifically described below, but the invention is not limited thereto. Compounding amounts are % by weight, unless otherwise described. The effect testing methods and evaluation methods used in the examples are as described below.

Hair Loss Prevention Effect Test

This effect was judged by determining the change in the number of hairs lost during hair washing, before and after use of the sample. Eight persons were tested as a group for each of Comparative examples 1, 2 and 3, and 4 persons were tested as a group for each of Examples 1 to 3. The test period was 6 months, in which the sample was not used for the first 2 months, and was used during the last 4 months. During the period in which the sample was used, the sample was applied to the scalp twice a day, in an amount of 2 to 4 ml for each application. During the test period, the hair was washed every other day, fallen hairs were recovered, and the total number of the fallen hairs for each week was counted. The total 8 data of the number of fallen hairs on the 2 months no sample application period, and the total 8 data of the number of fallen hairs on the last 2 months sample application period were arranged on each period, respectively, and the number of fallen hairs during each period was expressed as the number of fallen hairs per the period, in terms of the average value±standard deviation. The judgment of the effect was made according to the following criterion, based on the difference in average values obtained in the respective periods;

++: remarkable effect observed with the number of fallen hairs being reduced by 70 or more, +: considerable effect observed with the number of fallen hairs being reduced by 40 or more, ±: slight effect observed with the number of fallen hairs being reduced by 10 or more, −: no effect observed with the number of fallen hairs being reduced by less than 10.

Hair Revitalizing Effect Test

To determine the hair revitalizing effect of the hair revitalizing composition of this invention, the trichogram test was carried out. Five persons were tested as a group for each of Comparative examples 1, 2 and 3, and 4 persons were tested as a group for each of Examples 1 to 3. The sample was applied for 3 months, during which the sample was applied to the scalp twice a day, in an amount of 2 to 4 ml for each application. Immediately before the application and after the 3 months application, 50 hairs were pulled out per each person from the parietal region, respectively, the hair roots of the pulled out hairs were observed by a microscope, and the hair root resting period ratio (%) was calculated based on the form of the hair roots. The hair revitalizing effect of each sample was judged by increase or decrease of the hair root resting period ratio (%) between before and after application of the sample.

+: remarkable effect

±: weak effect

−: no effect

Dandruff and Itch Prevention Effect Test

Four persons were tested as a group of each of the examples and comparative examples. The sample was applied for 3 months, during which the hair was washed once a day with the same shampoo containing no pharmaceutical, and the test sample was applied to the scalp twice a day, in an amount of 2 to 4 ml for each application. At the time of completion of the period, dandruff on the head was collected by an aspirating device from the persons tested, and the amount of protein in the dandruff was measured. Further, after completion of the test period, the itch of the scalp of the persons tested was examined, and the extent of the itch was expressed according to the following scores.

Strong itch . . . 3
Some itch . . . 2
Slight itch . . . 1
No itch . . . 0

Examples 1 to 6 and Comparative examples 1 to 3

The formulations of Examples 1 to 6 and Comparative examples 1, 2 and 3 are shown in Table 1. The results of the hair loss prevention effect test of Examples 1 to 6 and Comparative examples 1, 2 and 3 are shown in Tables 2 and 3, the results of the hair revitalizing effect test of Examples 1 to 6 and Comparative examples 1, 2 and 3 are shown in Tables 4 and 5, and the results of the dandruff and itch prevention effect test of Examples 1 to 6 and Comparative examples 1, 2 and 3 are shown in Table 6.

TABLE 1

Formulation of composition

| | Comparative example | | | Example | | | | | |
|---|---|---|---|---|---|---|---|---|---|
| | 1 | 2 | 3 | 1 | 2 | 3 | 4 | 5 | 6 |
| N,N-Dimethyl-2-decyl-tetradecylamine oxide | — | — | 1.0 | 1.0 | 1.0 | 1.0 | 3.0 | 3.0 | 3.0 |
| N,N-Dimethyl-lauryl amine oxide | — | 1.0 | — | 0.4 | 0.5 | 1.0 | — | — | — |
| N-Ethyl-N-methyl-laurylamine oxide | — | — | — | — | — | — | 1.0 | — | — |
| N,N-Dihydroxyethyl-laurylamine oxide | — | — | — | — | — | — | — | 1.5 | — |
| N,N-Dimethyl-lauryl-polyoxyethylene (10 mols addition) amine oxide | — | — | — | — | — | — | — | — | 2.0 |
| 95% ethanol | 75.0 | 75.0 | 75.0 | 75.0 | 75.0 | 75.0 | 75.0 | 75.0 | 75.0 |
| Purified water | balance | balance | balance | balance | balance | balance | balance | balance | balance |
| mM ratio of compounds (formula (1)/(2)) | — | — | — | 4.34 | 3.47 | 1.73 | 4.9 | 2.75 | 0.92 |

TABLE 2

Hair loss prevention effect (comparison)

| | | Number of fallen hairs | | |
|---|---|---|---|---|
| Group | Person No. | No application period | Application period | Judgement |
| Comparative example 1 | 1 | 138 ± 21 | 141 ± 23 | — |
| | 2 | 411 ± 50 | 418 ± 58 | — |
| | 3 | 389 ± 20 | 346 ± 14 | + |
| | 4 | 250 ± 42 | 239 ± 39 | ± |
| | 5 | 168 ± 14 | 201 ± 31 | — |
| | 6 | 377 ± 76 | 386 ± 58 | — |
| | 7 | 324 ± 40 | 334 ± 45 | — |
| | 8 | 491 ± 64 | 476 ± 55 | ± |
| Comparative example 2 | 1 | 264 ± 38 | 218 ± 26 | + |
| | 2 | 328 ± 80 | 304 ± 39 | ++ |
| | 3 | 362 ± 38 | 368 ± 32 | — |
| | 4 | 281 ± 30 | 278 ± 28 | — |
| | 5 | 148 ± 21 | 139 ± 13 | — |
| | 6 | 196 ± 18 | 180 ± 19 | ± |
| | 7 | 235 ± 28 | 220 ± 40 | ± |
| | 8 | 486 ± 48 | 490 ± 48 | — |
| Comparative example 3 | 1 | 327 ± 42 | 274 ± 38 | + |
| | 2 | 192 ± 11 | 201 ± 17 | — |
| | 3 | 473 ± 66 | 328 ± 54 | ++ |
| | 4 | 514 ± 74 | 437 ± 58 | ++ |
| | 5 | 308 ± 26 | 261 ± 11 | + |
| | 6 | 334 ± 27 | 347 ± 30 | — |
| | 7 | 259 ± 39 | 242 ± 53 | ± |
| | 8 | 224 ± 14 | 179 ± 21 | ± |

TABLE 3

Hair loss prevention effect (this invention)

| Group | Person No. | Number of fallen hairs No application period | Application period | Judgement |
|---|---|---|---|---|
| Example 1 | 1 | 355 ± 33 | 312 ± 31 | + |
|  | 2 | 289 ± 42 | 213 ± 45 | ++ |
|  | 3 | 319 ± 25 | 325 ± 26 | − |
|  | 4 | 326 ± 32 | 309 ± 34 | ± |
| Example 2 | 1 | 348 ± 34 | 276 ± 35 | ++ |
|  | 2 | 167 ± 18 | 137 ± 16 | + |
|  | 3 | 499 ± 47 | 364 ± 41 | ++ |
|  | 4 | 282 ± 27 | 211 ± 25 | ++ |
| Example 3 | 1 | 138 ± 19 | 144 ± 18 | − |
|  | 2 | 508 ± 53 | 392 ± 45 | ++ |
|  | 3 | 336 ± 62 | 291 ± 59 | + |
|  | 4 | 295 ± 37 | 251 ± 40 | + |
| Example 4 | 1 | 427 ± 49 | 409 ± 53 | ± |
|  | 2 | 384 ± 45 | 299 ± 43 | ++ |
|  | 3 | 155 ± 20 | 142 ± 21 | ± |
|  | 4 | 205 ± 27 | 133 ± 15 | ++ |
| Example 5 | 1 | 149 ± 20 | 102 ± 13 | + |
|  | 2 | 572 ± 75 | 438 ± 44 | ++ |
|  | 3 | 382 ± 27 | 287 ± 26 | ++ |
|  | 4 | 351 ± 44 | 334 ± 41 | ± |
| example 6 | 1 | 158 ± 14 | 117 ± 11 | + |
|  | 2 | 217 ± 24 | 176 ± 18 | + |
|  | 3 | 415 ± 52 | 420 ± 43 | − |
|  | 4 | 434 ± 34 | 341 ± 31 | ++ |

TABLE 4

Hair revitalizing effect (comparison)

| Group | Person No. | Hair root resting ratio (%) Immediately before application | After application | Judgement |
|---|---|---|---|---|
| Comparative example 1 | 1 | 21.5 | 20.9 | − |
|  | 2 | 40.8 | 37.2 | ± |
|  | 3 | 15.7 | 15.9 | − |
|  | 4 | 28.4 | 28.9 | − |
|  | 5 | 26.3 | 28.5 | − |
| Comparative example 2 | 1 | 38.6 | 28.0 | + |
|  | 2 | 28.4 | 27.6 | − |
|  | 3 | 30.6 | 31.2 | − |
|  | 4 | 24.8 | 20.0 | + |
|  | 5 | 20.4 | 21.6 | − |
| Comparative example 3 | 1 | 11.8 | 13.9 | − |
|  | 2 | 36.5 | 28.2 | + |
|  | 3 | 34.2 | 30.9 | ± |
|  | 4 | 20.9 | 13.3 | + |
|  | 5 | 26.7 | 15.4 | + |

TABLE 5

Hair revitalizing effect (this invention)

| Group | Person No. | Hair root resting ratio (%) Immediately before application | After application | Judgement |
|---|---|---|---|---|
| Example 1 | 1 | 26.5 | 23.1 | ± |
|  | 2 | 19.5 | 10.1 | + |
|  | 3 | 23.4 | 16.2 | + |
|  | 4 | 31.8 | 27.0 | + |
| Example 2 | 1 | 40.3 | 33.8 | + |
|  | 2 | 31.2 | 30.2 | + |
|  | 3 | 20.1 | 11.5 | + |
|  | 4 | 22.8 | 18.1 | + |
| Example 3 | 1 | 25.4 | 20.6 | + |
|  | 2 | 19.3 | 19.2 | − |
|  | 3 | 19.7 | 13.4 | + |
|  | 4 | 33.8 | 19.6 | + |
| Example 4 | 1 | 26.6 | 22.1 | ± |
|  | 2 | 18.5 | 12.9 | + |
|  | 3 | 43.8 | 29.7 | + |
|  | 4 | 30.3 | 21.6 | + |
| Example 5 | 1 | 23.9 | 18.0 | + |
|  | 2 | 16.5 | 13.1 | ± |
|  | 3 | 38.8 | 30.5 | + |
|  | 4 | 31.5 | 25.7 | + |
| Example 6 | 1 | 22.3 | 15.1 | + |
|  | 2 | 15.6 | 12.5 | ± |
|  | 3 | 17.7 | 8.8 | + |
|  | 4 | 34.9 | 28.0 | + |

TABLE 6

Dandruff and itch prevention effect

| Group | Average amount of dandruff (mg) | Itch (average score) |
|---|---|---|
| Comparative example 1 | 18.26 | 2.0 |
| Comparative example 2 | 16.00 | 1.8 |
| Comparative example 3 | 13.08 | 1.3 |
| Example 1 | 6.93 | 0.5 |
| Example 2 | 4.88 | 0.25 |
| Example 3 | 7.15 | 1.0 |
| Example 4 | 8.49 | 0.5 |
| Example 5 | 5.03 | 0.25 |
| Example 6 | 7.26 | 0.5 |

Examples 7 to 15 and Comparative examples 4 to 10

The formulations of Examples 7 to 15 and Comparative examples 4 to 10 are shown in Table 7. The results of the hair loss prevention effect test obtained using the compositions of Comparative examples 4 to 7 and the compositions of Examples 7 to 9 are shown in Tables 8 and 9, respectively, the results of the hair revitalizing effect test of the compositions of Comparative examples 4 to 7 and the compositions of Examples 7 to 9 are shown in Tables 10 and 11, respectively, and the results of the dandruff and itch prevention effect test of the compositions of Comparative examples 4 to 10 and the compositions of Examples 7 to 15 are shown in Table 12.

TABLE 7

Formulation of composition

| | Comparative example | | | | | | |
|---|---|---|---|---|---|---|---|
| | 4 | 5 | 6 | 7 | 8 | 9 | 10 |
| N-Dimethyl-2-stearyl-eicosylamine oxide | — | — | — | 1.0 | — | 0.3 | — |
| N,N-Dimethyl-2-decyl-tetradecylamine oxide | — | — | 1.0 | — | 2.0 | — | 0.1 |
| N,N-Dimethyl-laurylamine oxide | — | 1.0 | — | — | — | — | — |
| N-Methyl-dilaurylamine oxide | — | — | — | — | 0.2 | — | — |
| N,N-Dihydroxyethyl-laurylamine oxide | — | — | — | — | — | 1.5 | — |
| N,N-Dimethyl-laurylpolyoxy-ethylene (10 mols) amine oxide | — | — | — | — | — | — | 2.0 |
| 95% Ethanol | 75.0 | 75.0 | 75.0 | 75.0 | 75.0 | 75.0 | 75.0 |
| Purified water | balance | balance | balance | balance | balance | balance | balance |
| mM ratio of compounds formula (1)/(2) | — | — | — | — | 10.37 | 0.39 | 0.03 |

| | Example | | | | | | | | |
|---|---|---|---|---|---|---|---|---|---|
| | 7 | 8 | 9 | 10 | 11 | 12 | 13 | 14 | 15 |
| N-Dimethyl-2-stearyl-eicosylamine oxide | — | — | — | — | — | — | 1.0 | — | 0.5 |
| N,N-Dimethyl-2-decyl-tetradecylamine oxide | 1.0 | 1.0 | 1.0 | 3.0 | 3.0 | 3.0 | 1.0 | 1.0 | 0.5 |
| N,N-Dimethyl-laurylamine oxide | 0.4 | 0.5 | 1.0 | — | — | — | — | 0.1 | 0.2 |
| N-Methyl-dilaurylamine oxide | — | — | — | 0.7 | — | — | 0.6 | — | — |
| N,N-Dihydroxyethyl-laurylamine oxide | — | — | — | — | 1.5 | — | — | 0.2 | — |
| N,N-Dimethyl-lauryl-olyoxyethylene (10 mols) amine oxide | — | — | — | — | — | 2.0 | — | — | 0.2 |
| 95% Ethanol | 75.0 | 75.0 | 75.0 | 75.0 | 75.0 | 75.0 | 75.0 | 75.0 | 75.0 |
| Purified water | balance | balance | balance | balance | balance | balance | balance | balance | balance |
| mM ratio of compounds formula (1)/(2) | 4.33 | 3.47 | 1.73 | 4.44 | 2.75 | 0.92 | 4.19 | 4.92 | 2.74 |

TABLE 8

Hair loss prevention effect (comparison)

| | | Number of fallen hairs | | |
|---|---|---|---|---|
| Group | Person No. | No application period | Application period | Judgement |
| Comparative example 4 | 1 | 249 ± 39 | 252 ± 35 | − |
| | 2 | 312 ± 13 | 300 ± 24 | ± |
| | 3 | 301 ± 48 | 307 ± 53 | − |
| | 4 | 199 ± 27 | 153 ± 29 | + |
| | 5 | 178 ± 37 | 159 ± 35 | ± |
| | 6 | 395 ± 42 | 314 ± 28 | ++ |
| | 7 | 512 ± 53 | 459 ± 36 | + |
| | 8 | 286 ± 34 | 298 ± 27 | − |
| Comparative example 5 | 1 | 227 ± 31 | 173 ± 28 | + |
| | 2 | 367 ± 29 | 344 ± 21 | ± |
| | 3 | 502 ± 58 | 498 ± 28 | − |
| | 4 | 197 ± 43 | 203 ± 38 | − |
| | 5 | 331 ± 18 | 283 ± 21 | + |
| | 6 | 384 ± 27 | 404 ± 38 | − |
| | 7 | 163 ± 21 | 153 ± 18 | ± |
| | 8 | 288 ± 29 | 238 ± 27 | + |
| Comparative example 6 | 1 | 281 ± 27 | 285 ± 24 | − |
| | 2 | 371 ± 40 | 362 ± 38 | − |
| | 3 | 258 ± 28 | 180 ± 22 | ++ |
| | 4 | 525 ± 29 | 501 ± 33 | ± |
| | 5 | 221 ± 17 | 233 ± 24 | − |
| | 6 | 183 ± 21 | 142 ± 18 | + |
| | 7 | 319 ± 30 | 320 ± 35 | − |
| | 8 | 442 ± 45 | 434 ± 39 | − |
| Comparative example 7 | 1 | 318 ± 22 | 324 ± 31 | − |

TABLE 8-continued

Hair loss prevention effect (comparison)

| | | Number of fallen hairs | | |
|---|---|---|---|---|
| Group | Person No. | No application period | Application period | Judgement |
| | 2 | 384 ± 43 | 351 ± 33 | ± |
| | 3 | 243 ± 28 | 256 ± 38 | − |
| | 4 | 307 ± 19 | 253 ± 30 | + |
| | 5 | 226 ± 24 | 185 ± 24 | + |
| | 6 | 423 ± 34 | 420 ± 29 | − |
| | 7 | 364 ± 33 | 339 ± 28 | ± |
| | 8 | 289 ± 22 | 271 ± 33 | ± |

TABLE 9

Hair loss prevention effect (this invention)

| | | Number of fallen hairs | | |
|---|---|---|---|---|
| Group | Person No. | No application period | Application period | Judgement |
| Example 7 | 1 | 286 ± 30 | 213 ± 28 | ++ |
| | 2 | 312 ± 33 | 235 ± 31 | ++ |
| | 3 | 299 ± 19 | 276 ± 21 | ± |
| | 4 | 426 ± 37 | 377 ± 51 | + |
| Example 8 | 1 | 307 ± 28 | 255 ± 39 | + |
| | 2 | 413 ± 31 | 363 ± 61 | + |
| | 3 | 444 ± 40 | 341 ± 38 | ++ |
| | 4 | 287 ± 36 | 281 ± 34 | − |
| example 9 | 1 | 523 ± 39 | 450 ± 53 | ++ |
| | 2 | 378 ± 42 | 318 ± 31 | + |
| | 3 | 199 ± 22 | 177 ± 18 | ± |
| | 4 | 263 ± 36 | 179 ± 31 | ++ |

TABLE 10

Hair revitalizing effect (comparison)

| | | Hair root resting ratio (%) | | |
|---|---|---|---|---|
| Group | Person No. | Immediately before application | After application | Judgement |
| Comparative example 4 | 1 | 13.7 | 14.3 | − |
| | 2 | 28.5 | 30.2 | − |
| | 3 | 30.4 | 21.3 | + |
| | 4 | 29.8 | 28.8 | − |
| | 5 | 15.6 | 12.2 | ± |
| Comparative example 5 | 1 | 35.1 | 25.6 | + |
| | 2 | 24.4 | 26.7 | − |
| | 3 | 15.2 | 20.3 | − |
| | 4 | 28.8 | 25.4 | ± |
| | 5 | 12.5 | 9.5 | ± |
| Comparative example 6 | 1 | 22.2 | 18.6 | ± |
| | 2 | 41.6 | 45.8 | − |
| | 3 | 33.9 | 32.6 | − |
| | 4 | 12.6 | 8.9 | ± |
| | 5 | 19.9 | 20.2 | − |
| Comparative example 7 | 1 | 25.4 | 27.7 | − |
| | 2 | 31.7 | 23.1 | + |
| | 3 | 19.1 | 19.0 | − |
| | 4 | 17.7 | 13.9 | ± |
| | 5 | 28.5 | 30.3 | − |

TABLE 11

Hair revitalizing effect (this invention)

| | | Hair root resting ratio (%) | | |
|---|---|---|---|---|
| Group | Person No. | Immediately before application | After application | Judgement |
| Example 7 | 1 | 28.3 | 19.5 | + |
| | 2 | 19.2 | 16.8 | ± |
| | 3 | 14.7 | 7.9 | + |
| | 4 | 41.1 | 28.5 | + |
| Example 8 | 1 | 23.8 | 20.9 | ± |
| | 2 | 24.1 | 21.1 | ± |
| | 3 | 38.6 | 33.2 | + |
| | 4 | 15.4 | 10.1 | + |
| Example 9 | 1 | 18.6 | 12.3 | + |
| | 2 | 30.2 | 20.5 | + |
| | 3 | 34.3 | 26.6 | + |
| | 4 | 21.5 | 12.3 | + |

TABLE 12

Dandruff and itch prevention effect

| Group | Average amount of dandruff (mg) | Itch (average score) |
|---|---|---|
| Comparative example 4 | 18.26 | 2.0 |
| Comparative example 5 | 16.00 | 1.8 |
| Comparative example 6 | 13.08 | 1.3 |
| Comparative example 7 | 15.01 | 1.8 |
| Comparative example 8 | 18.34 | 2.0 |
| Comparative example 9 | 12.06 | 1.3 |
| Comparative example 10 | 20.18 | 1.8 |
| Example 7 | 6.93 | 0.5 |
| Example 8 | 4.88 | 0.25 |
| Example 9 | 7.15 | 1.0 |
| Example 10 | 8.49 | 0.5 |
| Example 11 | 5.03 | 0.25 |
| Example 12 | 7.26 | 0.5 |
| Example 13 | 5.33 | 0.5 |
| Example 14 | 7.91 | 0.75 |
| Example 15 | 8.66 | 0.25 |

Examples 16 to 21 and Comparative examples 11 and 12

These examples and comparative examples are for illustrating the influence of the compounding ratio between N,N-dimethyl-2-decyl-tetradecylamine oxide (hereafter abbreviated as "$C_{24}AO$") belonging to the compounds of the formula (1) and N,N-dimethyl-2-laurylamine oxide (hereafter abbreviated as "$C_{12}AO$") belonging to the compounds of the formula (2) on hair revitalizing effect.

The hair revitalizing test used in these examples and comparative examples are as follows.
Hair Revitalizing Effect Assay Method (Assay of hair revitalizing effect in mice)

Experiment was carried out according to the method of Ogawa et al. (Normal and Abnormal Epidermal Differentiation, edited by M. Seiji and I. A. Barstein, published by Todai Shuppan-kai), using male C3H mice (60 days after birth). Namely, hair on the back of each mouse was shaved into a size of about 2×4 cm. Samples were applied every day once a day to the mice, respectively, from the next day, and change of the area ratio of the part where hair regeneration began was checked on each mouse, and thereby the speeds of hair regeneration were compared. Each sample was obtained by dissolving each amine oxide in 75% ethanol under stirring. 10 mice were used for each sample, and the average value of the change rate was calculated. The result of hair regeneration area after the time lapse of 30 days was expressed by percentage.

Test composition

The concentrations of $C_{24}AO/C_{12}AO$ were adjusted to zero (0)/30 mM (Comparative Example 11), 10 mM/20 mM (Example 16), 15 mM/15 mM (Example 17), 20 mM/10 mM (Example 18), 22 mM/8 mM (Example 19), 24 mM/6 mM (Example 20), 25 mM/5 mM (Example 21), and 30 mM/zero (0) (Comparative Example 12) with 75% ethanol, respectively. The results of the hair revitalizing effect test on these compositions are shown in FIG. 1.

Example 22

This example is for illustrating the influence of the difference in carbon numbers between the long-chain aliphatic groups in amine oxides to be combined together on hair revitalizing effect.

Hair regeneration areas (%) obtained when the hair revitalizing test stated in the above Examples 16 to 21 was used are shown below. Compositions used in the test were prepared by adjusting the concentrations of amine oxides used to those described below with 75% ethanol, respectively, and dissolving the amine oxides.

TABE 13

| Example No. | Compound of the formula (1) (concentration) | Compound of the formula (2) (concentration) | Hair regeneration area (%) |
|---|---|---|---|
| (this invention) | | | |
| 22 | $C_{22}AO$ (10 mM) | $C_{16}AO$ (5 mM) | 78 |
| 23 | $C_{24}AO$ (10 mM) | $C_{18}AO$ (5 mM) | 85 |
| 24 | $C_{24}AO$ (10 mM) | $C_{18F}AO$ (5 mM) | 95 |
| 25 (Comparative example No.) | $C_{30}AO$ (10 mM) | $C_{14}AO$ (5 mM) | 80 |
| 13 | $C_{22}AO$ (10 mM) | $C_{20}AO$ (10 mM) | 52 |
| 14 | $C_{24}AO$ (10 mM) | $C_{20}AO$ (10 mM) | 56 |

$C_{22}AO$: N,N-Dimethyl-2-decyldodecylamine oxide
$C_{24}AO$: N,N-Dimethyl-2-decyltetradecylaniine oxide
$C_{30}AO$: N,N-Dimethyl-2-decyleicosylamine oxide
$C_{16}AO$: N,N-Dimethyl-2 hexyldecy amine oxide
$C_{18}AO$: N,N-Dimethyl-2-octcyldodecylamine oxide
$C_{18F}AO$: N,N-Dimethyl-oleylamine oxide
$C_{20}AO$: N,N-Dimethyl-eicosylamine oxide
$C_{14}AO$: N,N-Dimethyl-myristylamine oxide

Example 23

A lotion having the following composition was prepared.

| | |
|---|---|
| 95% Ethanol | 50.0 |
| Monoammonium glycyrrhetate | 0.1 |
| N,N-dimethyl-2-decyltetradecyl-amine oxide | 1.0 |
| N,N-dimethyl-laurylamine oxide | 0.5 |
| Sodium lauryl sulfate | 0.06 |
| Hardened castor oil-ethylene oxide (40 mols) adduct | 0.5 |
| Succinic acid | appropriate amount |
| Perfume and coloring matter | appropriate amount |
| Purified water | balance |

(Preparation process)

The hardened castor oil-ethylene oxide (40 mols) adduct and perfume were dissolved in 95% ethanol, purified water was added, the other components were then added, and the mixture was stirred for dissolution to give a transparent liquid lotion.

Example 24

A lotion having the following composition was prepared.

| | |
|---|---|
| 95% Ethanol | 90.0 |
| Vitamin E acetate | 0.05 |
| N,N-dimethyl-2-decyltetradecyl-amine oxide | 3.0 |
| N,N-dihydroxyethyl-lauryl-amine oxide | 1.5 |
| Sodium lauryl sulfate | 0.06 |
| Propylene glycol | 0.1 |
| Hardened castor oil-ethylene oxide (40 mols) adduct | 0.5 |
| Malic acid | appropriate amount |
| Perfume and coloring matter | appropriate amount |
| Purified water | balance |

(Preparation process)

The hardened castor oil-ethylene oxide (40 mols) adduct and perfume were dissolved in 95% ethanol, purified water was added, the other components were then added, and the mixture was stirred for dissolution to give a transparent liquid lotion.

The compositions of Examples 23 and 24 were excellent in hair loss prevention effect and hair revitalizing effect, and also excellent in dandruff and itch prevention effect.

What is claimed is:

1. A hair revitalizing composition comprising as an effective ingredient a combination of at least one amine oxide compound represented by the formula (1-a):

(1-a)

wherein $R^{2-a}$ is a branched chain $C_{22-36}$ alkyl; and at least one amine oxide compound represented by the formula (2-e):

(2-e)

wherein $R^{4-e}$ is a straight-chain or branched chain $C_{12-20}$ alkyl or alkenyl, and the difference in carbon numbers between the group $R^{2-a}$ of said at least one compound according to the formula (1-a) and the group $R^{4-a}$ of said at least one compound according to the formula (2-e) being 6 or more, and the molar ratio of the compound of the above formula (1-a) to the compound of the above formula (2-e) being within the range of 0.5 to 5.

2. The hair revitalizing composition according to claim 1, wherein the branched chain $C_{22-36}$ alkyl in the compound of the formula (1-a) is a compound having one $C_{10-18}$ alkyl at the 2-position of another alkyl as a substituent.

3. The hair revitalizing composition according to claim 1, wherein the amine oxide compound other than the compound of the formula (1-a) is selected from the group consisting of compounds represented by the following formula:

wherein $R^{4-e}$ is as defined above.

4. The hair revitalizing composition according to claim 1, wherein the branched chain $C_{22-36}$ alkyl in the compound of the formula (1-a) is a compound having one $C_{10-18}$ alkyl at the 2-position of another alkyl as a substituent, and the amine oxide compound other than the compound of the formula (1-a) is represented by the formula (2-e); and wherein the difference in carbon numbers between the group $R^{2-a}$ of said at least one compound according to the formula (1-a) and the group $R^{4-e}$ of said at least one compound according to the formula (2-e) is 8 to 14.

5. The hair revitalizing composition according to claim 1, wherein the molar ratio of the compound of the above formula (1-a) to the compound of the above formula (2-e) is within the range of 0.8 to 2.5.

6. The hair revitalizing composition according to claim 1, wherein the molar ratio of the compound of the above formula (1-a) to the compound of the above formula (2-e) is within the range of 1 to 1.7.

7. The hair revitalizing composition according to claim 1, wherein the compound of the formula (1-a) is selected from the group consisting of N,N-dimethyl-2-decyldodecylamine oxide, N,N-dimethyl-2-decyltetradecylamine oxide, N,N-dimethyl-2-decylhexadecylamine oxide, N,N-dimethyl-2-octyleicosylamine oxide and N,N-dimethyl-2-decyleicosylamine oxide; and the compound of the formula (2-e) is selected from the group consisting of N,N-dimethyl-laurylamine oxide, N,N-dimethyl-myristylamine oxide, N,N-dimethyl-2-hexyldecylamine oxide, N,N-dimethyl-2-octyldecylamine oxide, N,N-dimethyl-oleylamine oxide and N,N-dimethyl-eicosylamine oxide.

8. The hair revitalizing composition according to claim 1, wherein the combination of at least one amine oxide compound of the formula (1-a) and at least one amine oxide compound of the formula (2-e) is selected from the group consisting of N,N-dimethyl-2-decyltetradecylamine oxide and N,N-dimethyl-laurylamine oxide; N,N-dimethyl-2-decyldodecylamine oxide and N,N-dimethyl-2-hexyldecylamine oxide; N,N-dimethyl-2-decyltetradecylamine oxide and N,N-dimethyl-2-octyldecylamine oxide; N,N-dimethyl-2-decyltetradecylamine oxide and N,N-dimethyl-oleylamine oxide; N,N-dimethyl-2-decyleicosylamine oxide and N,N-dimethyl-myristylamine oxide; and N,N-dimethyl-2-octylstearylamine oxide and N,N-dimethyl-oleylamine oxide.

9. A hair revitalizing method of applying a hair revitalizing composition in an effective amount for hair revitalization to the scalp or skin of a mammal, wherein said hair revitalizing composition is a hair revitalizing composition comprising as an effective ingredient a combination of at least one amine oxide compound represented by the formula (1-a):

wherein $R^{2-a}$ is a branched chain $C_{22-36}$ alkyl; and at least one amine oxide compound represented by the formula (2-e):

wherein $R^{4-e}$ is a straight-chain or branched chain $C_{12-20}$ alkyl or alkenyl, and the difference in carbon numbers between the group $R^{2-a}$ of said at least one compound according to the formula (1-a) and the group $R^{4-e}$ of said at least one compound according to the formula (2-e) being 6 or more, and the molar ratio of the compound of the above formula (1-a) to the compound of the above formula (2-e) being within the range of 0.5 to 5.

10. A method for preparing a hair revitalization composition comprising combining at least one amine oxide compound represented by the formula (1-a):

wherein $R^{2-a}$ is a branched chain $C_{22-36}$ alkyl; and at least one amine oxide compound represented by the formula (2-e):

wherein $R^{4-e}$ is a straight-chain or branched chain $C_{12-20}$ alkyl or alkenyl, and the difference in carbon numbers between the group $R^{2-a}$ of said at least one compound according to the formula (1-a) and the group $R^{4-e}$ of said at least one compound according to the formula (2-e) being 6 or more, and the molar ratio of the compound of the above formula (1-a) to the compound of the above formula (2-e) being within the range of 0.5 to 5.

* * * * *